(12) United States Patent
Ueda et al.

(10) Patent No.: US 10,654,933 B2
(45) Date of Patent: May 19, 2020

(54) METHOD FOR PURIFYING ANTIBODY HAVING LOW ISOELECTRIC POINT

(71) Applicant: Chugai Seiyaku Kabushiki Kaisha, Kita-ku, Tokyo (JP)

(72) Inventors: Yasufumi Ueda, Kita-ku (JP); Shohei Kobayashi, Kita-ku (JP); Satoko Yanagita, Kita-ku (JP); Takuo Kawase, Kita-ku (JP); Masahiro Fukunaga, Kita-ku (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 439 days.

(21) Appl. No.: 15/108,017

(22) PCT Filed: Dec. 26, 2014

(86) PCT No.: PCT/JP2014/084671
§ 371 (c)(1),
(2) Date: Jun. 24, 2016

(87) PCT Pub. No.: WO2015/099165
PCT Pub. Date: Jul. 2, 2015

(65) Prior Publication Data
US 2016/0326253 A1 Nov. 10, 2016

(30) Foreign Application Priority Data
Dec. 27, 2013 (JP) ................................ 2013-271613

(51) Int. Cl.
| C07K 1/22 | (2006.01) |
| C07K 1/18 | (2006.01) |
| C07K 1/36 | (2006.01) |
| B01D 15/38 | (2006.01) |
| C07K 16/28 | (2006.01) |
| A61K 39/395 | (2006.01) |
| C07K 16/00 | (2006.01) |

(52) U.S. Cl.
CPC .... *C07K 16/2866* (2013.01); *A61K 39/39591* (2013.01); *C07K 1/18* (2013.01); *C07K 1/22* (2013.01); *C07K 1/36* (2013.01); *C07K 16/00* (2013.01); *C07K 2317/14* (2013.01); *C07K 2317/24* (2013.01)

(58) Field of Classification Search
None
See application file for complete search history.

(56) References Cited

U.S. PATENT DOCUMENTS

| 4,891,312 A * | 1/1990 | Schaumann ....... C07K 16/3046 435/7.4 |
| 8,367,586 B2 | 2/2013 | Urlinger et al. |
| 2009/0324589 A1 | 12/2009 | Igawa et al. |
| 2010/0135987 A1 | 6/2010 | Hickman et al. |
| 2011/0245473 A1 | 10/2011 | Igawa et al. |
| 2012/0129717 A1 | 5/2012 | Urlinger et al. |
| 2012/0201814 A1 | 8/2012 | McKinnon et al. |
| 2014/0206845 A1 | 7/2014 | Kameoka et al. |
| 2015/0110793 A1 | 4/2015 | Shiraiwa et al. |

FOREIGN PATENT DOCUMENTS

| CA | 2731220 A1 * | 1/2010 | ......... C07K 16/2818 |
| CN | 101874042 A | 10/2010 | |
| CN | 102257005 A | 11/2011 | |
| CN | 103237809 A | 8/2013 | |
| EP | 2 202 245 A1 | 6/2010 | |
| EP | 2735315 A1 | 5/2014 | |
| JP | 05-504579 A | 7/1993 | |
| JP | 08-510116 A | 10/1996 | |
| JP | 2010-517942 A | 5/2010 | |
| JP | 2010-528588 A | 8/2010 | |
| JP | 2010-241761 A | 10/2010 | |
| JP | 2010-536037 A | 11/2010 | |
| JP | 2011-528551 A | 11/2011 | |
| JP | 2012-504106 A | 2/2012 | |
| JP | 2013-524773 A | 6/2013 | |
| JP | 2013-538051 A | 10/2013 | |
| JP | 2013-545452 A | 12/2013 | |
| RU | 2409591 C2 | 1/2011 | |
| RU | 2011/120191 A | 11/2012 | |
| WO | WO 92/07084 A1 | 4/1992 | |

(Continued)

OTHER PUBLICATIONS

Fahrner et al. "Industrial Purification of Pharmaceutical Antibodies: Development, Operation, and Validation of chromatography processes" Biotechnology and Genetic Engineering Reviews, 18, Jul. 2001 (Year: 2001).*

Gagnon, Pete, "Technology trends in antibody purification," Journal of Chromatography A, Jan. 20, 2012 (Epub Oct. 20, 2011), 1221:57-70.

Jungbauer et al., "Scaleup of Monoclonal Antibody Purification Using Radial Streaming Ion Exchange Chromatography," Biotechnology and Bioengineering, Jul. 20, 1988, 32(3):326-333.

*Primary Examiner* — Daniel E Kolker
*Assistant Examiner* — James L Rogers
(74) *Attorney, Agent, or Firm* — Foley & Lardner LLP

(57) ABSTRACT

The present inventors discovered that additional aggregation of low-pI antibody can be suppressed by removing formed antibody aggregates after a certain period of time following Protein A column purification, acidic treatment, and neutralization. Furthermore, the present inventors found that efficient impurities removal for a low-pI antibody can be accomplished by using an anion exchange resin in the Bind/Elute mode and then a hydrophobic interaction chromatography or multimodal chromatography resin, compared with conventional methods.

11 Claims, No Drawings

Specification includes a Sequence Listing.

(56) References Cited

FOREIGN PATENT DOCUMENTS

| | | |
|---|---|---|
| WO | WO 94/24163 A2 | 10/1994 |
| WO | WO 2005/044856 A1 | 5/2005 |
| WO | WO 2005/077130 A2 | 8/2005 |
| WO | WO 2007/114319 A1 | 10/2007 |
| WO | WO 2008/086335 A2 | 7/2008 |
| WO | WO 2008/143954 A2 | 11/2008 |
| WO | WO 2009/023457 A1 | 2/2009 |
| WO | WO 2009/041621 A1 | 4/2009 |
| WO | WO 2010/009391 A1 | 1/2010 |
| WO | WO-2010/048192 A2 | 4/2010 |
| WO | WO 2010/106812 A1 | 9/2010 |
| WO | WO 2010/141039 A1 | 12/2010 |
| WO | WO 2011/106528 A1 | 9/2011 |
| WO | WO 2012/025618 A1 | 3/2012 |
| WO | WO 2012/051147 A | 4/2012 |
| WO | WO 2012/058592 A2 | 5/2012 |
| WO | WO 2013/012022 A1 | 1/2013 |
| WO | WO 2013/096322 A1 | 6/2013 |
| WO | WO 2013/100120 A1 | 7/2013 |

\* cited by examiner

METHOD FOR PURIFYING ANTIBODY HAVING LOW ISOELECTRIC POINT

CROSS-REFERENCE TO RELATED APPLICATIONS

This application is a National Stage application of PCT/JP2014/084671, filed Dec. 26, 2014, which claims priority from Japanese application JP 2013-271613, filed Dec. 27, 2013.

TECHNICAL FIELD

The present invention relates to methods for purifying an antibody, and in particular, purification methods for an antibody with a low isoelectric point (pI).

BACKGROUND ART

With development of genetic recombination techniques, various protein formulations have become available in stable supply. Specifically, in recent years, various therapeutic antibodies with higher selectivity than that of conventional medicinal products have been developed by genetic recombination techniques and have entered clinical trials.

For drug products containing a biologically active protein produced by such genetic recombination techniques, it is necessary to remove host cell-derived proteins (host cell proteins) and DNA, resin ligand fragments which are one of the raw materials in purification, and aggregates or fragments derived from the protein of interest. Furthermore, to ensure safety of the drug products against viruses, the purification step must be shown to have a sufficient ability to remove or inactivate viruses. Currently, the World Health Organization (WHO) indicates that the acceptable amount of DNA in a biological medicinal product is 100 pg DNA/dose or less. Furthermore, the World Health Organization (WHO) indicates that regarding viruses, if the presence of retrovirus-like particles is observed in the cultured solution, the drug product may contain no more than one virus particle per $10^6$ doses after taking into account the ability to remove or inactivate retroviruses in the purification step. Generally, to meet this criterion, impurities are removed by treating the aqueous cultured medium containing the bioactive protein obtained from the host cells with affinity chromatography, cation exchange chromatography, anion exchange chromatography, hydroxyapatite chromatography, or hydrophobic interaction chromatography, or a combination thereof. Furthermore, development of new purification ligands has advanced in recent years, and multimodal chromatography that has two functions of both the ion-exchanging action and hydrophobic interaction is also used for purification.

In particular, when the bioactive protein is an antibody that can be obtained by using mammalian cells as the host, it is purified by treatment with the Protein A or Protein G affinity column chromatography by utilizing the property of Protein A or Protein G to bind to the Fc region of IgG, followed by various chromatography methods.

For example, in Japanese Patent Application Kohyo Publication No. (JP-A) H05-504579 (unexamined Japanese national phase publication corresponding to a non-Japanese international publication) (Patent Document 1), an antibody-containing aqueous cultured medium obtained from a mammalian cell culture was subjected to a protein A or protein G column chromatography to absorb the antibody to the column, the antibody was then eluted using an acidic solution (citric acid at a concentration of approximately 0.1 M at pH 3.0-3.5), and the resulting acidic eluate was purified by subsequent ion-exchange column chromatography and size exclusion column chromatography.

In order to increase the blood retention or in vivo kinetics, amino acid substitution techniques for controlling the isoelectric point (pI) of an antibody, specifically the technique of altering amino acid residue(s) exposed on the surface of an antibody to control the pI of the antibody (WO 07/114319 (Patent Document 2)) are known. The isoelectric point (pI) of a native antibody is in the range of approximately 7.5-9.5 and is a relatively high pI. Lowering the pI by modifying the amino acid residues of such an antibody is expected to prolong the plasma retention and half-life of the antibody, and this will lead to reduction in the amount of antibody administered as a drug and extension of the administration intervals.

However, until now, there has been no investigation on purification methods that are appropriate for low-pI antibodies which do not exist in nature, or examination of issues specific to low-pI antibodies in the purification process. Therefore, nothing is known with respect to purification methods that are suitable for such low-pI antibodies.

PRIOR ART DOCUMENTS

Patent Documents

[Patent Document 1] Japanese Patent Application Kohyo Publication No. (JP-A) H05-504579 (unexamined Japanese national phase publication corresponding to a non-Japanese international publication)
[Patent Document 2] WO 07/114319

SUMMARY OF THE INVENTION

Problems to be Solved by the Invention

An objective of the present invention is to provide antibody purification methods that can efficiently remove impurities from, in particular, a composition containing a low-pI antibody.

In general, as a method to roughly purify the antibodies from a cultured medium, it is mainstream to use a protein A column. In this case, it is common to use an acidic solution in the step of eluting the product from the column, carry out a virus inactivation by holding an acidic condition for a predetermined period of time by further adding an acid as required, and then move on to the next purification process immediately after neutralization.

The present inventors found that in particular when an antibody modified to have a low pI is purified by a normal purification process, there is a problem of additional formation of aggregates after the purification process is completed. As a result of root cause analysis, the present inventors discovered the phenomena that when an antibody is placed under an acidic condition for a certain period of time and then neutralized, some of the antibodies gradually aggregate irreversibly for a certain period of time.

General antibodies have a high pI and are basic; and they are therefore purified using a Protein A affinity chromatography resin, followed by purification using a cation exchange chromatography resin in bind/elute mode, and an anion exchange chromatography resin in pass-through mode due to their basic property. Usually, cation exchange chromatography resins are known to remove aggregates, and anion exchange chromatography resins are known to remove impurities such as DNA, host cell proteins, and viruses through adsorption. However, as a result of investigation to purify the low pI engineered antibodies, the conventional purification methods were found to be insufficient to remove impurities contained in the antibody cultured medium.

Means for Solving the Problems

As a result of dedicated research to achieve the above-mentioned objective, the present inventors discovered that additional aggregation of low-pI antibody can be suppressed by removing formed antibody aggregates after a certain period of time following Protein A column purification and neutralization.

Furthermore, the present inventors found that using an anion exchange chromatography resin in the Bind/Elute mode to purify a low-pI antibody enables more efficient removal of impurities than by conventional methods. Furthermore, they discovered that further removal of impurities becomes possible by using multimodal chromatography or hydrophobic interaction chromatography in addition to anion exchange chromatography.

More specifically, the present invention provides the following [1] to [19]:
[1] a method for purifying a composition containing an antibody with a pI of 3.0 to 8.0, which comprises the steps of:
(a) treating the composition containing the antibody with a pI of 3.0 to 8.0 with an acidic condition;
(b) neutralizing the acidic composition obtained in step (a); and
(c) removing aggregates from the neutralized composition obtained in step (b) after at least one hour following the neutralization;
[2] the method of [1], wherein step (a) is a virus-inactivating treatment step performed after purification of the antibody with a pI of 3.0 to 8.0 by Protein A column chromatography;
[3] the method of [1] or [2], wherein step (c) is a step of removing aggregates after holding the neutralized composition obtained in step (b) for at least one hour following the neutralization;
[4] the method of any one of [1] to [3], wherein the aggregate removal is carried out by anion exchange chromatography, hydrophobic interaction chromatography, multimodal chromatography, or hydroxyapatite chromatography;
[5] the method of any one of [1] to [4], wherein the pI of the antibody is 5.0 to 7.5;
[6] the method of any one of [1] to [4], wherein the pI of the antibody is 5.0 to 6.5;
[7] a method for removing an impurity from a composition containing an antibody with a pI of 3.0 to 8.0, which comprises the steps of:
(a) loading the composition containing the antibody with a pI of 3.0 to 8.0 onto an anion exchange chromatography resin; and
(b) eluting the antibody with a pI of 3.0 to 8.0 from the anion exchange resin with the Bind/Elute mode using an eluting solution that has higher salt concentration than that of the composition of (a);
[8] the method of [7], which comprises the step of washing the anion exchange resin with a washing solution before step (b);
[9] the method of [7] or [8], wherein the eluting solution of step (b) is a solution containing at least one selected from the group consisting of sodium chloride, Tris salt, sodium sulfate salt, and sodium phosphate salt;
[10] the method of any one of [7] to [9], which further comprises the step of loading the elution product containing the antibody with a pI of 3.0 to 8.0 obtained in step (b) onto chromatography that uses a resin containing a hydrophobic ligand and/or a multimodal ligand, and obtaining a Flow-through fraction and/or an elution fraction;
[11] the method of any one of [1] to [6], wherein an aggregates removal is carried out by the method of any one of [7] to [10];
[12] the method of any one of [1] to [11], wherein the antibody is a humanized antibody or a human antibody;
[13] the method of any one of [1] to [12], wherein the antibody is an anti-IL-6 receptor antibody or an anti-IL-31 receptor antibody;
[14] a method for producing a composition containing an antibody with a pI of 3.0 to 8.0, in which the content ratio of the antibody aggregates is 3% or less, by the method of any one of [1] to [13];
[15] a composition containing an antibody with a pI of 3.0 to 8.0, in which the content ratio of the antibody aggregates is 3% or less;
[16] a composition containing an antibody with a pI of 3.0 to 8.0 produced by the method of [14], in which the content ratio of the aggregate is 3% or less;
[17] a method for producing a pharmaceutical composition containing an antibody with a pI of 3.0 to 8.0, which comprises the steps of:
1) producing an antibody with a pI of 3.0 to 8.0 and/or a composition containing such an antibody by the production method of [14]; and
2) formulating the antibody with a pI of 3.0 to 8.0 and/or the composition containing such an antibody produced in step 1) by mixing it with a pharmaceutically acceptable carrier and/or additive;
[18] a method for removing an antibody aggregate from a composition containing an antibody with a pI of 3.0 to 8.0, which includes the steps of:
(a) treating the composition containing an antibody with a pI of 3.0 to 8.0 with an acidic condition;
(b) neutralizing the acidic composition obtained in step (a); and
(c) removing aggregates from the neutralized composition obtained in step (b) after at least one hour following the neutralization; and
[19] a method for purifying a composition containing an antibody with a pI of 3.0 to 8.0, which comprises the steps of:
(a) treating the composition containing an antibody with a pI of 3.0 to 8.0 with an acidic condition;
(b) neutralizing the acidic composition obtained in step (a); and
(c) removing aggregates from the neutralized composition obtained in step (b) after a sufficient time has passed for aggregates formation.

MODE FOR CARRYING OUT THE INVENTION

Herein below, the present invention will be specifically described.

The present invention relates to a method for removing the antibody aggregates and impurities from a composition containing an antibody with a low isoelectric point (pI). Specifically, the present invention relates to a method for removing aggregates from a composition containing an antibody with a pI of 3.0 to 8.0, which comprises the steps of:

(a) treating the composition comprising an antibody with a pI of 3.0 to 8.0 with an acidic condition;
(b) neutralizing the acidic composition obtained in step (a); and
(c) removing aggregates from the neutralized composition obtained in step (b) after at least one hour following the neutralization.

In the present invention, additional aggregates formation after purification can be suppressed by removing aggregates from the composition after sufficient time has passed for aggregates formation in the neutralized composition obtained in step (b).

Specifically, additional aggregates formation after purification can be suppressed by removing aggregates from the neutralized composition obtained in step (b) after at least one hour has passed following the neutralization.

More specifically, step (c) of the present invention can be reworded as follows:
removing the aggregates from the neutralized composition obtained in step (b) after sufficient time has passed for aggregates formation;
removing aggregates from the composition after aggregates formation reaches at least 80% or more relative to the amount of aggregates that may be formed in the neutralized composition obtained in step (b);
removing aggregates from the composition after aggregates formation reaches at least 80% or more relative to the amount of aggregates that may be formed after the neutralized composition obtained in step (b) is held for at least 24 hours;
removing aggregates from the composition after completion of 80% or more of aggregates formation that may take place in the neutralized composition obtained in step (b); and
removing aggregates from the composition at least one hour before completion of aggregate formation in the neutralized composition obtained in step (b).

Furthermore, the present invention relates to a method for removing impurities from a composition containing an antibody with a pI of 3.0 to 8.0, which comprises the steps of:
(a) loading the composition containing an antibody with a pI of 3.0 to 8.0 onto an anion exchange chromatography resin; and
(b) eluting the antibody with a pI of 3.0 to 8.0 from the anion exchange chromatography resin in the Bind/Elute mode using an eluting solution that has a salt concentration higher than that of the composition of (a).

In the above-mentioned method, a step of washing the anion exchange chromatography resin using a washing solution can be included before step (b).

In the present invention, the method for removing antibody aggregates from a composition containing the antibody with a pI of 3.0 to 8.0 can also be expressed as a method for purifying an antibody (antibody monomer) from a composition containing the antibody with a pI of 3.0 to 8.0, a method for removing impurities from a composition containing an antibody with a pI of 3.0 to 8.0, a method for suppressing aggregation of an antibody with a pI of 3.0 to 8.0, or such.

Furthermore, the method for removing impurities from a composition containing an antibody with a pI of 3.0 to 8.0 may also be expressed as a method for purifying an antibody (antibody monomer) from a composition containing an antibody with a pI of 3.0 to 8.0, a method for removing antibody aggregates from a composition containing an antibody with a pI of 3.0 to 8.0, or such.

In the present invention, the composition containing an antibody may also be expressed as an antibody-containing solution, antibody culture solution, antibody culture medium, or such.

Antibodies used in the present invention are not particularly limited as long as they bind to the desired antigens; and while they may be polyclonal antibodies or monoclonal antibodies, monoclonal antibodies are preferred since they enable stable production of homogeneous antibodies.

The monoclonal antibodies used in the present invention include not only those derived from animals such as humans, mice, rats, hamsters, rabbits, sheep, camels, and monkeys, but also artificially engineered recombinant antibodies such as chimeric antibodies, humanized antibodies, and bispecific antibodies. These antibodies also include recombinant antibodies that result from artificially engineering the antibody constant regions and such to alter the physical properties of the antibody molecule (specifically, alteration of the isoelectric point (pI), alteration of the Fc receptor affinity, etc.) for the purpose of increasing blood retention or in vivo kinetics.

The immunoglobulin class of the antibodies used in the present invention is not particularly limited, and the class may be any class, including IgG such as IgG1, IgG2, IgG3, and IgG4, IgA, IgD, IgE, and IgM. However, IgG and IgM are preferred.

The antibodies used in the present invention also include not only antibodies that have constant regions and variable regions (whole antibodies) but also antibody fragments such as Fv, Fab, and F(ab)$_2$, and low-molecular-weight antibodies (minibodies) such as mono-, bi-, or multi-valent single-chain Fv (scFv, sc(Fv)$_2$) that result from linking antibody variable regions via a linker such as peptide linker, and diabodies such as scFv dimer; however, whole antibodies are preferred.

The above-described antibodies used in the present invention can be prepared by methods known to those skilled in the art. Basically, monoclonal antibody-producing hybridomas can be prepared by using known techniques such as those described below. More specifically, immunization is carried out by a conventional immunization method using a desired antigen or cells expressing the desired antigen as a sensitizing antigen. The resulting immune cells are fused with known parental cells by a conventional cell fusion method. The fused cells are screened for monoclonal antibody-producing cells (hybridomas) by conventional screening methods to produce the antibodies. Hybridomas can be generated, for example, according to the method of Milstein et al. (Kohler, G. and Milstein, C., Methods Enzymol. (1981) 73: 3-46). When an antigen has low immunogenicity, immunization can be performed by linking the antigen to an immunogenic macromolecule such as albumin.

Alternatively, it is possible to use recombinant antibodies produced using gene recombination techniques in which antibody genes are cloned from hybridomas and inserted into appropriate vectors, and the resulting vectors are introduced into hosts (see, for example, Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, cDNAs for antibody variable regions (V regions) are synthesized from mRNAs of the hybridomas using reverse transcriptase. When a DNA encoding an antibody V region of interest is obtained, the DNA is linked to a DNA encoding a desired antibody constant region (C region). The resulting construct is inserted into an expression vector. Alternatively, the antibody V region-encoding DNA may be inserted into an expression vector carrying the DNA of the antibody C region. The resulting construct is inserted into an expression vector so that it is expressed under the control of an expression regulatory region, for example, an enhancer or a promoter. Then, host cells are transformed with the expression vector to express the antibody.

In the present invention, artificially modified recombinant antibodies, for example, chimeric and humanized antibodies can be used to reduce heterologous antigenicity against humans, and such. Such modified antibodies can be produced using known methods. A chimeric antibody is an antibody consisting of the heavy-chain and light-chain variable regions of an antibody from a non-human mammal such as mouse, and the heavy-chain and light-chain constant regions of a human antibody. The chimeric antibody can be obtained by linking a DNA encoding the variable regions of a mouse antibody to a DNA encoding the constant regions of a human antibody, inserting it into an expression vector, and then introducing the vector into a host to produce the antibody.

A humanized antibody is also referred to as a reshaped human antibody, and is obtained by transplanting the complementarity determining region (CDR) of an antibody derived from a non-human mammal such as mouse into the complementarity determining region of a human antibody. Its general gene recombination techniques are known. Specifically, a DNA sequence is designed to have a mouse antibody CDR linked to a human antibody framework region (FR), and is synthesized by PCR using several oligonucleotides prepared to have overlapping portions at their ends. The obtained DNA is ligated to a DNA encoding a human antibody constant region and then inserted into an expression vector. The expression vector is introduced into a host to produce the humanized antibody (see European Patent Application Publication No. EP 239400 and WO 96/02576). The CDR-linked human antibody FR is selected so that the complementarity determining region forms a preferable antigen-binding site. Amino acids in the framework region of the antibody variable region can be substituted as required so that the complementarity determining region of the reshaped human antibody forms a suitable antigen-binding site (Sato, K. et al., Cancer Res. (1993) 53, 851-856).

Techniques for substituting amino acid(s) in an antibody to increase activities, physical properties, pharmacokinetics, safety, and such of the antibody are known, and examples of such techniques are described below. The antibodies used in the present invention also include those having such amino acid substitutions (and including also deletions and additions).

Techniques have been reported for substituting amino acid(s) in the IgG antibody variable regions, and include humanization (Tsurushita N, Hinton P R, Kumar S., Design of humanized antibodies: from anti-Tac to Zenapax., Methods. 2005 May; 36(1): 69-83); affinity maturation to enhance the binding activity via amino acid substitution in the complementarity determining region (CDR) (Rajpal A, Beyaz N, Haber L, Cappuccilli G, Yee H, Bhatt R R, Takeuchi T, Lerner R A, Crea R., A general method for greatly improving the affinity of antibodies by using combinatorial libraries., Proc Natl Acad Sci USA. 2005 Jun. 14; 102(24): 8466-71); and improvement of physicochemical stability via amino acid substitution in the framework (FR) (Ewert S, Honegger A, Pluckthun A., Stability improvement of antibodies for extracellular and intracellular applications: CDR grafting to stable frameworks and structure-based framework engineering., Methods. 2004 October; 34(2): 184-99. Review). There are also known techniques for enhancing antibody-dependent cellular cytotoxicity (ADCC) and complement-dependent cytotoxicity (CDC) by substituting amino acid(s) in the IgG antibody Fc region (Kim S J, Park Y, Hong H J., Antibody engineering for the development of therapeutic antibodies., Mol Cells. 2005 Aug. 31; 20(1): 17-29. Review). Furthermore, in addition to such techniques for enhancing effector functions, there are reports on techniques for increasing the antibody half-life in blood by substituting amino acid(s) in Fc (Hinton P R, Xiong J M, Johlfs M Cc Tang M T, Keller S, Tsurushita N., An engineered human IgG1 antibody with longer serum half-life., J Immunol. 2006 Jan. 1; 176(1): 346-56; Ghetie V, Popov S, Borvak J, Radu C, Matesoi D, Medesan C, Ober R J, Ward E S., Increasing the serum persistence of an IgG fragment by random mutagenesis., Nat. Biotechnol. 1997 July; 15(7): 637-40). Various techniques of substituting amino acid(s) in the constant regions for the purpose of increasing the physical properties of an antibody are also known (WO 09/41613).

Methods for obtaining human antibodies are also known. For example, desired human antibodies with antigen-binding activity can be obtained by sensitizing human lymphocytes in vitro with an antigen of interest or with cells expressing an antigen of interest; and fusing the sensitized lymphocytes with human myeloma cells such as U266 (see Japanese Patent Application Kokoku Publication No. (JP-B) H01-59878 (examined, approved Japanese patent application published for opposition)). Alternatively, desired human antibodies can also be obtained by immunizing transgenic animals having the entire repertoire of human antibody genes with an antigen (see WO 93/12227, WO 92/03918, WO 94/02602, WO 94/25585, WO 96/34096, and WO 96/33735). Furthermore, techniques for obtaining human antibodies by panning with a human antibody library are known. For example, the variable regions of human antibodies are expressed as single-chain antibodies (scFvs) on the surface of phages using a phage display method, and then phages that bind to the antigen can be selected. Genes of the selected phages can be analyzed to determine DNA sequences that encode the variable regions of the human antibodies that bind to the antigen. When the DNA sequences of scFvs that bind to the antigen are identified, appropriate expression vectors carrying these sequences can be constructed to obtain human antibodies. Such methods are already well known, and WO 92/01047, WO 92/20791, WO 93/06213, WO 93/11236, WO 93/19172, WO 95/01438, and WO 95/15388 can be used as reference. The antibodies used in the present invention also include such human antibodies.

When an antibody gene is isolated and then introduced into appropriate hosts to produce antibodies, hosts and expression vectors can be used in appropriate combinations. When eukaryotic cells are used as the host, animal cells, plant cells, and fungal cells can be used. Known animal cells include: (1) mammalian cells, for example, CHO, COS, myeloma, baby hamster kidney (BHK), HeLa, and Vero; (2) amphibian cells, for example, *Xenopus* oocytes; and (3) insect cells, for example, sf9, sf21, and Tn5. Known plant cells include cells derived from the genus *Nicotiana* such as *Nicotiana tabacum*, which can be cultured as a callus. Known fungal cells include yeasts such as the genus *Saccharomyces*, for example, *Saccharomyces cerevisiae*, and filamentous fungi such as the genus *Aspergillus*, for example, *Aspergillus niger*. When using prokaryotic cells, production systems using bacterial cells can be used. Known bacterial cells include *Escherichia coli* (*E. coli*) and *Bacillus subtilis*. Antibodies can be obtained by introducing the antibody genes of interest into these cells by transformation and then culturing the transformed cells in vitro.

The antibodies used in the present invention also include antibody fragments, minibodies, and antibody modification products. Antibody fragments and minibodies include, for example, Fab, F(ab')2, Fv, or mono-, bi-, or multi-valent single-chain Fv (scFv, sc(Fv)$_2$, or such) that result from linking the H chain and L chain Fvs via appropriate linkers (Huston J. S. et al., Proc. Natl. Acad. Sci. U.S.A. (1988) 85: 5879-5883). Specifically, such antibody fragments are generated by treating antibodies with an enzyme such as papain or pepsin. Alternatively, genes encoding these antibody fragments are constructed, inserted into expression vectors, and then expressed in appropriate host cells (see, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

Antibodies linked to various molecules such as polyethylene glycol (PEG) or cytotoxic agents may be used as antibody modification products (Farmaco. 1999 Aug. 30; 54(8): 497-516; Cancer J. 2008 May-June; 14(3): 154-69). The antibodies used in the present invention also include such antibody modification products. Such antibody modification products can be obtained by chemically modifying antibodies. Such methods are already established in this field.

Antibodies to be used in the present invention include, but are not limited to, anti-tissue factor antibodies, anti-IL-6 receptor antibodies, anti-IL-6 antibodies, anti-HM1.24 antigen monoclonal antibodies, anti-parathyroid hormone-related peptide antibodies (anti-PTHrP antibodies), anti-glypican-3 antibodies, anti-ganglioside GM3 antibodies, anti-TPO receptor agonist antibodies, antibodies substituting for coagulation factor VIII, anti-IL31 receptor antibodies, anti-HLA antibodies, anti-AXL antibodies, anti-CXCR4 antibodies, anti-NR10 antibodies, and bi-specific antibodies against factor IX and factor X.

Preferred reshaped humanized antibodies used in the present invention include humanized anti-interleukin 6 (IL-6) receptor antibodies (tocilizumab, hPM-1, or MRA) (see WO 92/19759), humanized anti-HM1.24 antigen monoclonal antibodies (see WO 98/14580), humanized anti-parathyroid hormone-related peptide antibodies (anti-PTHrP antibodies) (see WO 98/13388), humanized anti-tissue factor antibodies (see WO 99/51743), anti-glypican-3 humanized IgG1κ antibodies (see PCT/JP05/013103), anti-NR10 humanized antibodies (see WO 2009/072604), and bi-specific humanized antibodies against factor IX and factor X, but are not limited thereto. Particularly preferred humanized antibodies used in the present invention are humanized anti-IL-6 receptor antibodies, anti-NR10 humanized antibodies, and bi-specific humanized antibodies against factor IX and factor X.

Preferred human IgM antibodies include recombinant human anti-ganglioside GM3 IgM antibodies (see WO 05/05636).

Preferred minibodies include anti-TPO receptor agonist diabodies (see WO 02/33072) and anti-CD47 agonist diabodies (see WO 01/66737).

In the present invention, "antibodies with a low isoelectric point (low-pI antibodies)" refers to specifically antibodies that have a low isoelectric point, which hardly exist in nature. The isoelectric point of such antibodies may be, for example 3.0 to 8.0, preferably 5.0 to 7.5, more preferably 5.0 to 7.0, still more preferably 5.0 to 6.8, even more preferably 5.0 to 6.5, and particularly preferably 5.0 to 6.0, but are not limited thereto. Native (or ordinary) antibodies are considered to have an isoelectric point usually in the range of 7.5 to 9.5.

Furthermore, preferred antibodies to be used in the present invention include pI-modified antibodies, in which the amino acid residue(s) exposed on the antibody surface is/are modified to lower the pI of the antibodies. Such a pI-modified antibody refers to an antibody whose pI has been lowered by 1 or more, preferably 2 or more, and more preferably 3 or more as compared to the pI of the antibody before the modification. As described in the Examples below, the isoelectric point of Mab1, which was produced from modification of amino acid sequence of the Mab3 (isoelectric point: 9.4) to regulate the isoelectric point, was 5.8. Furthermore, the fully humanized NS22 antibody (isoelectric point: 7.8) produced by the method described in Example 12 of WO2009/072604 was subjected to modification of the amino acid sequence to regulate the isoelectric point, and the resulting Mab2 had an isoelectric point of 5.6.

Antibodies with an improved isoelectric point include, for example, Mab1 (H chain/SEQ ID NO: 1; L chain/SEQ ID NO: 2), which is an anti-IL-6 receptor antibody described in WO 2009/041621, anti-NR10 humanized antibodies, and fully humanized NS22 antibodies (H chain/SEQ ID NO: 3; L chain/SEQ ID NO: 4) produced by the method described in Example 12 of WO 2009/072604, but are not limited thereto.

In the case of an H-chain variable region, examples of amino acid residues exposed on the antibody surface include amino acid residues selected from among the amino acid residues at H1, H3, H5, H8, H10, H12, H13, H15, H16, H19, H23, H25, H26, H31, H39, H42, H43, H44, H46, H61, H62, H64, H65, H68, H71, H72, H73, H75, H76, H81, H82b, H83, H85, H86, H105, H108, H110, and H112 according to Kabat numbering, but are not limited thereto. In the case of an L-chain variable region, the examples are amino acid residues selected from among the amino acid residues at L1, L3, L7, L8, L9, L11, L12, L16, L17, L18, L20, L22, L24, L27, L38, L39, L41, L42, L43, L45, L46, L49, L53, L54, L55, L57, L60, L63, L65, L66, L68, L69, L70, L74, L76, L77, L79, L80, L81, L85, L100, L103, L105, L106, and L107 according to Kabat numbering, but are not limited thereto.

In the present invention, "modification" refers to substituting the original amino acid residue with another amino acid residue, deleting the original amino acid residue, adding a new amino acid residue, and such, but preferably, it refers to substitution of the original amino acid residue with another amino acid residue.

Some amino acids are known to be charged amino acids. Generally, lysine (K), arginine (R), and histidine (H) are known as positively charged amino acids (cationic amino acids). Aspartic acid (D), glutamic acid (E), and such are known as negatively charged amino acids (anionic amino acids). Amino acids other than these are known as uncharged amino acids.

In the present invention, preferably, the amino acid residues present after the modification are suitably selected from the amino acid residues included in either one of groups (a) and (b) below, without particular limitations thereto:

(a) glutamic acid (E) and aspartic acid (D); and
(b) lysine (K), arginine (R), and histidine (H).

In a preferred embodiment, if the amino acid residue before modification is already charged, it may be modified to be an uncharged amino acid residue.

More specifically, the modification in the present invention includes: (1) substitution of a charged amino acid with an uncharged amino acid; (2) substitution of a charged amino acid with an amino acid carrying a charge opposite to that of the original amino acid; and (3) substitution of an uncharged amino acid with a charged amino acid.

The value of an isoelectric point can be determined by isoelectric focusing known to those skilled in the art. Theoretical isoelectric point values can be calculated using a gene or amino acid sequence analysis software (for example, Genetyx).

Antibodies in which the charge of amino acid residues has been modified can be obtained by modifying nucleic acids encoding the antibodies, culturing those nucleic acids in host cells, and purifying the antibodies from the host cell culture. In the present invention, the phrase "modifying nucleic acids" refers to modifying nucleic acid sequences so that they become codons that correspond to amino acid residues introduced by the modification. More specifically, it refers to modifying the nucleotide sequence of a nucleic acid so that the codon encoding the original amino acid residue becomes a codon encoding the amino acid residue to be introduced by the modification. That is, a codon encoding the amino acid residue to be modified is replaced by a codon encoding the amino acid residue to be introduced by the modification. Such nucleic acid modifications can be carried out appropriately by those skilled in the art using known techniques, for example, site-directed mutagenesis or PCR mutagenesis.

In a preferred embodiment of the present invention, a method containing the following steps enables efficient removal of aggregates formed from a composition containing an antibody with a pI of 3.0 to 8.0:
(a) treating the composition containing an antibody with a pI of 3.0 to 8.0 with an acidic condition;
(b) neutralizing the acidic composition obtained in step (a); and
(c) removing aggregates from the neutralized composition obtained in step (b) after at least one hour following the neutralization.

Examples of the aggregates of an antibody with a pI of 3.0 to 8.0 in the present invention include 1.5-mers, dimers, trimers, tetramers, pentamers, and such, but are not limited thereto.

Methods of the present invention can efficiently remove aggregates of low-pI antibodies formed in a solution, and can suppress the risk of subsequent production of new aggregates. In the present invention, examples of the acidic condition for treating an antibody-containing composition include generally pH 2.0 to 4.0, preferably pH 3.0 to 3.9, and more preferably pH 3.1 to 3.8, but are not limited thereto.

The method for treating an antibody-containing composition with an acidic condition includes a method of adding known acids such as hydrochloric acid, citric acid, phosphoric acid, or acetic acid to an antibody-containing composition, but is not limited thereto.

In the present invention, the antibody-containing composition treated with an acidic condition is preferably held for a certain period of time. The holding time is, for example, 15 minutes to 4 hours, preferably 30 minutes to 2 hours, and more preferably 1 to 1.5 hours, but is not limited thereto.

In the present invention, the step of neutralizing an acidic composition refers to a step of neutralizing a composition containing an antibody with a pI of 3.0 to 8.0 and which has been subjected to an acidic treatment. The post-neutralization pH includes generally pH 4.5 to 8.5, preferably pH 6.5 to 8.5, and more preferably pH 7.0 to 8.5, but is not limited thereto.

The results of the Examples of this application elucidated that aggregates are formed each time when the above-mentioned step of increasing the pH of the acidic composition (such as the neutralization step) is performed intermittently in the antibody purification method of the present invention. Therefore, in the antibody purification method or aggregate removal method of the present invention, the step of removing the formed antibody aggregates is preferably performed after completion of the final pH-increasing step (such as a neutralization step). Furthermore, it is preferred that a step that increases the pH again is not performed after removing the aggregates.

Furthermore, in the present invention, when the antibody-containing acidic composition is neutralized and the composition is held for a certain period of time at a pH lower than the pI of the antibody, the step of adjusting the pH of the composition to a value higher than the pI of the antibody and holding this composition for a certain period of time can be further included. More specifically, the present invention relates to a method for purifying a composition containing an antibody with a pI of 3.0 to 8.0, which comprises the steps of:
(a) treating the composition containing an antibody with a pI of 3.0 to 8.0 with an acidic condition;
(b) neutralizing the acidic composition obtained in step (a), and holding the composition at a pH lower than the pI of the antibody; and
(c) adjusting the pH of the neutralized composition obtained in step (b) to a value higher than the pI of the antibody; and
(d) removing aggregates from the neutralized composition obtained in step (b) after at least one hour following neutralization. Examples of a pH lower than the pI of an antibody include, but are not limited to, a pH lower than the pI of the antibody by 0.3 or more, preferably 0.5 or more, and more preferably 1.0 or more. On the other hand, examples of a pH higher than the pI of an antibody include, but are not limited to, a pH higher than the pI of the antibody by 0.3 or more, preferably 0.5 or more, and more preferably 1.0 or more. Furthermore, examples of the length of time the neutralized composition is held include, but are not limited to, 1 hour or longer (for example, 1 hour to 7 days, preferably 1 to 3 days), preferably 2 hours or longer (for example, 2 hours to 7 days, preferably 2 hours to 72 hours), more preferably 6 hours or longer (for example, 6 hours to 7 days, preferably 6 hours to 72 hours), and even more preferably 12 hours or longer (for example, 12 hours to 7 days, preferably 12 hours to 72 hours).

Neutralization can be carried out using a buffer. The buffer used for the neutralization is not particularly limited as long as it is a buffer commonly used for pH adjustment, and examples include, but are not limited to, Tris and disodium hydrogen phosphate, and Tris is preferred.

The present invention is characterized by the novel finding that after neutralization of an antibody-containing acidic solution, irreversible aggregate formation continues for a certain period of time. Such phenomenon has not been observed in ordinary antibodies with unmodified pI (antibodies with a pI around 9). While the reason why irreversible aggregates are formed is unclear, this phenomenon may be caused by stress to the low-pI antibody in an acidic solution, adjustment of the pH of the composition near the antibody pI, and charge change of the antibody molecule by pH adjustment of the composition across the antibody pI. Either way, in the methods of the present invention, after a certain amount of time has passed following neutralization of an acid-treated antibody with a pI of 3.0 to 8.0, the formed antibody aggregates are removed to prevent production of new aggregates after aggregate removal.

More specifically, the length of time until aggregates of the neutralized antibody are removed is generally one hour or longer (for example, 1 hour to 7 days, preferably 1 to 3 days), preferably 2 hours or longer (for example, 2 hours to 7 days, preferably 2 hours to 72 hours), more preferably 6 hours or longer (for example, 6 hours to 7 days, preferably 6 hours to 72 hours), even more preferably 12 hours or longer (for example, 12 hours to 7 days, preferably 12 hours to 72 hours), and particularly preferably 20 hours, 23 hours, 24 hours, 66 hours, or longer, but is not limited thereto.

Alternatively, in the present invention, after sufficient time has passed for aggregate formation, the aggregates are removed from the neutralized composition. In the present invention, "sufficient time for aggregate formation" refers to the time required for antibodies that are expected of aggregate formation in a neutralized composition to form aggregates. Sufficient time for aggregate formation of the present invention includes not only the time required for all antibodies expected of aggregate formation to form aggregates, but also the time required to form aggregates in at least 50% or more, preferably 70% or more, more preferably 80% or more, and particularly preferably 90% or more of the antibodies expected of aggregate formation. By taking account into the time for aggregate formation shown in Example 1, those skilled in the art can determine the length of time until aggregates of antibody are removed after neutralization.

Alternatively, in the present invention, aggregates can be removed from a neutralized composition after aggregate formation reaches at least 50% or more, preferably 70% or more, more preferably 80% or more, and particularly preferably 90% or more relative to the amount of aggregates that may form in the composition. In the present invention, the amount of aggregates that may form in a neutralized composition refers to the amount of aggregates formed by antibodies that are expected to form aggregates in the neutralized composition. Examples of the amount of aggregates that may form in a neutralized composition include, but are not limited to, the amount of aggregates formed after the composition is held for generally 1 hour or longer (for example, 1 hour to 7 days, preferably 1 to 3 days), preferably 2 hours or longer (for example, 2 hours to 7 days, preferably 2 hours to 72 hours), more preferably 6 hours or longer (for example, 6 hours to 7 days, preferably 6 hours to 72 hours), and particularly preferably 24 hours following neutralization.

Alternatively, in the present invention, aggregates can be removed from a neutralized composition after at least 50% or greater, preferably 70% or greater, more preferably 80% or greater, and particularly preferably 90% or greater of the possible aggregate formation that may take place in the composition is completed. In the present invention, the possible aggregate formation that may take place in a neutralized composition refers to aggregate formation by antibodies that are expected to form aggregates.

Alternatively, in the present invention, aggregates can be removed from a neutralized composition at least one hour before completion of aggregate formation in the composition. In the present invention, "completion of aggregate formation" refers to completion of aggregate formation by antibodies that are expected to form aggregates. Completion of aggregate formation in the present invention refers not only to aggregate formation by all antibodies that are expected to form aggregates, but also completion of aggregate formation by at least 50% or more, preferably 70% or more, more preferably 80% or more, and particularly preferably 90% or more of the antibodies that are expected to form aggregates.

Whether antibody aggregate formation is completed can be investigated by, for example, analyzing a neutralized composition of the present invention over time by size exclusion chromatography (SEC) after neutralization and plotting the amount of the formed aggregates, as in the method shown in the later-described Examples.

In the present invention, the formed aggregates can be removed by known methods using anion exchange chromatography, multimodal chromatography, hydrophobic interaction chromatography, hydroxyapatite chromatography, and such. The use of anion exchange chromatography or hydroxyapatite chromatography is particularly preferred.

Furthermore, aggregates of the present invention can be removed efficiently by using a purification step with anion exchange chromatography in bind/elute mode to be described later.

The anion exchange resin in the present invention is not limited as long as it shows an anion exchange action. The anion exchange resin includes, but is not limited to:
YMC-BioPro (YMC Co. Ltd.);
Q Sepharose High Performance (GE Healthcare);
Q Sepharose Fast Flow (GE Healthcare);
Q Sepharose XL (GE Healthcare);
Capto Q ImpRes (GE Healthcare);
Capto Q (GE Healthcare);
Capto DEAE (GE Healthcare);
SOURCE 30Q (GE Healthcare);
SOURCE 15Q (GE Healthcare);
POROS HQ (Life Technologies, Inc.);
POROS D (Life Technologies, Inc.);
POROS PI (Life Technologies, Inc.);
Eshumuno Q (Merck Millipore Corp.);
Fractogel TMAE (Merck Millipore Corp.);
Fractogel DEAE (Merck Millipore Corp.);
Macro-Prep Q (Bio-Rad Laboratories Inc.);
Macro-Prep DEAE (Bio-Rad Laboratories Inc.);
Giga Cap Q-650M (TOSOH Corp.);
Giga Cap DEAE-650M (TOSOH Corp.); and
Q HyperCel (PALL Corp.).

Furthermore, examples of resins for hydroxyapatite column chromatography include, but are not limited to,
Ceramic Hydroxyapatite (Bio-Rad Laboratories Inc.);
Ceramic Fluoloapatite (Bio-Rad Laboratories Inc.);
MPC Ceramic Hydroxyfluoloapatite (Bio-Rad Laboratories Inc.); and
HA Ultragel (PALL Corp.).

Examples of resins for multimodal chromatography include, but are not limited to,
Capto Adhere (GE Healthcare);
Capto MMC (GE Healthcare); and
Eshumuno HCX (Merck Millipore Corp.).

Examples of resins for hydrophobic interaction chromatography include, but are not limited to,
Phenyl Sepharose High Performance (GE Healthcare);
Butyl Sepharose High Performance (GE Healthcare);
Phenyl Sepharose 6 Fast Flow (GE Healthcare);
Butyl-S Sepharose 6 Fast Flow (GE Healthcare);
Butyl Sepharose 4 Fast Flow (GE Healthcare);
Octyl Sepharose 4 Fast Flow (GE Healthcare);
Capto Phenyl ImpRes (GE Healthcare);

Capto Phenyl (GE Healthcare);
Capto Butyl (GE Healthcare);
Capto Octyl (GE Healthcare);
Fractogel Phenyl (Merck Millipore Corp.);
Fractogel Propyl (Merck Millipore Corp.);
TOYOPEARL Butyl (TOSOH Corp.);
TOYOPEARL Ether (TOSOH Corp.);
TOYOPEARL Hexyl (TOSOH Corp.);
TOYOPEARL Phenyl (TOSOH Corp.);
TOYOPEARL PPG (TOSOH Corp.);
TOYOPEARL SuperButyl (TOSOH Corp.);
TOYOPEARL Butyl-600 (TOSOH Corp.); and
Macro-Prep HIC (Bio-Rad Laboratories Inc.).

Whether the aggregates are removed can be determined by methods known to those skilled in the art such as size exclusion chromatography (SEC), without being limited thereto.

In the present invention, the antibody-containing composition treated with an acidic condition may be a composition purified by known purification methods such as Protein A column chromatography. That is, the method for removing aggregates of the present invention may include "a step of purifying the composition containing an antibody with a pI of 3.0 to 8.0 by Protein A column chromatography" before "(a) the step of treating the composition containing an antibody with a pI of 3.0 to 8.0 with an acidic condition".

Furthermore, in the present invention, after steps (a) to (c) described above for removing aggregates of antibodies with a pI of 3.0 to 8.0, the later-described step of purification by anion exchange chromatography in bind/elute mode, and/or the step of purification by multimodal chromatography in flow-through mode or hydrophobic interaction chromatography in flow-through mode can be included. When these steps are combined, an antibody with a pI of 3.0 to 8.0 can be purified efficiently, including removal of impurities other than the aggregates.

More specifically, the present invention relates to a method for efficiently removing impurities from a composition containing an antibody with a pI of 3.0 to 8.0 by a method containing the steps of:
(a) loading the composition containing an antibody with a pI v of 3.0 to 8.0 onto an anion exchange resin; and
(b) eluting the antibody with a pI of 3.0 to 8.0 from the anion exchange resin in bind/elute mode using an eluting solution that has a salt concentration higher than that of the composition of (a).

In the above-mentioned method, an additional step of washing the anion exchange resin using a washing solution can be included before step (b).

As described later, in the present invention, the fraction eluted from the anion exchange resin can be further subjected to multimodal chromatography or hydrophobic interaction chromatography. This enables further removal of impurities.

The impurity to be removed may be any substance as long as it is not the protein of interest. Examples of the impurity include, but are not limited to, host cell-derived proteins (host cell proteins) and DNA, Protein A (leached from column), fragments and aggregates derived from the protein of interest, viruses, endotoxins, medium component Hy-Fish (FL), IGF, insulin, antibiotics, and anti-foaming agents. Preferably, but without limitation, host cell proteins and DNA, Protein A, aggregates derived from the protein of interest (for example, antibody aggregates), and viruses can be removed in the present invention.

Viruses removed by the method of the present invention are not particularly limited. Viruses of the present invention include DNA viruses and RNA viruses. Without limitation, DNA viruses include parvoviruses such as MVM, and RNA viruses include retroviruses such as MuLV and reoviruses such as Reo 3. Specific examples of the viruses removed by the method of the present invention include, but are not limited to, viruses such as MuLV, PRV, Reo 3, MVM, SV40, VSV, herpes simplex, CHV, sindbis, mumps, vaccinia, Measle, Rubella, influenza, herpes zoster, cytomegalo, parainfluenza, EB, HIV, HA, HB, NANB, ATL, ECHO, and parvo; and are preferably viruses such as MuLV, Reo 3, MVM, PRV, and SV40, without being limited thereto.

In the present invention, the characteristics of low-pI antibodies were utilized for the first time to establish a method of purifying antibodies using an anion column in bind/elute mode, which could not be accomplished for conventional antibodies having a relatively high pI. Furthermore, by combined use of this with multimodal chromatography or hydrophobic interaction chromatography, a purification method that enables further removal of impurities was established for the first time.

In the methods of the present invention, as conditions for purifying a composition containing an antibody with a pI of 3.0 to 8.0 by an anion exchange resin, ordinarily a column equilibrated with a buffer having a pH of 6 to 9, which is Tris, BIS-TRIS, and histidine at a concentration of 1 mmol/L to 100 mmol/L with addition of chloride ions and acetate ions as the counter ions is used. Preferably, but without limitation, the purification is carried out using a column equilibrated with a buffer having a pH of 7 to 8, which is Tris at a concentration of 10 mmol/L to 50 mmol/L with addition of chloride ions or acetate ions as the counter ions.

Next, the methods of the present invention may include a step of washing the anion exchange resin to which the antibodies with a pI of 3.0 to 8.0 have been adsorbed. Washing is performed in a condition similar to general equilibration condition or using a buffer having an equivalent or higher pH or a lower concentration relative to those of buffers in an elution condition. Specifically, washing is performed using a column equilibrated with a buffer having a pH of 6 to 9, which is Tris, BIS-TRIS, and histidine at a concentration of 1 mmol/L to 100 mmol/L with addition of chloride ions and acetate ions as the counter ions. Preferably, but without limitation, the washing is carried out using a buffer having a pH of 7 to 8, which is Tris at a concentration of 10 mmol/L to 50 mmol/L with addition of chloride ions or acetate ions as the counter ions.

Next, in the methods of the present invention, antibodies are eluted from an anion exchange resin in bind/elute mode using an eluting solution that has a salt concentration higher than that of the composition containing an antibody with a pI of 3.0 to 8.0. The conditions for elution normally involve the use of a buffer having a pH of 6 to 9, which is Tris, BIS-TRIS, and histidine at a concentration of 1 mmol/L to 500 mmol/L with addition of chloride ions and acetate ions as the counter ions, and further addition of sodium chloride, potassium chloride, sodium sulfate, and sodium phosphate as necessary. Preferably, but without limitation, elution is performed using a buffer having a pH of 7 to 8, which is Tris at a concentration of 10 mmol/L to 500 mmol/L with addition of chloride ions or acetate ions as the counter ions, and further addition of sodium chloride, sodium phosphate, and sodium sulfate at 50 mmol/L to 500 mmol/L as necessary. Examples of a salt concentration higher than that of the composition containing an antibody with a pI of 3.0 to 8.0 include, but are not limited to, 5 mmol/L or higher, and preferably 10 mmol/L or higher. The eluting solution includes, but are not limited to, solutions containing at least one selected from the group consisting of sodium chloride, Tris salt, sodium sulfate, and sodium phosphate.

In the present invention, the eluted fraction (eluate) containing the antibody with a pI of 3.0 to 8.0 obtained from the anion exchange resin can be purified further by multimodal chromatography (for example, resins having the functions of both hydrophobic interaction and anion exchange action).

Purification of antibody-containing compositions by multimodal chromatography resins is generally performed using a buffer having a pH of 4 to 9, which is Tris, BIS-TRIS, and histidine at a concentration of 1 mmol/L to 500 mmol/L with addition of chloride ions and acetate ions as the counter ions, and further addition of sodium chloride, potassium chloride, sodium sulfate, ammonium sulfate, sodium citrate, and arginine as necessary. Preferably, but without limitation, purification is performed using a column equilibrated with a buffer having a pH of 6 to 7, which is Tris at a concentration of 10 mmol/L to 500 mmol/L with addition of chloride ions or acetate ions as the counter ions, and further addition of sodium chloride and/or sodium sulfate at 50 mmol/L to 500 mmol/L as necessary.

The fraction containing the antibody of interest with pI of 3.0 to 8.0 can be obtained as flow-through fraction and/or the elution fraction of multimodal chromatography by loading the eluted fraction from anion exchange chromatography obtained by the method of the present invention. Normally, the load fraction is adjusted in advance to have a pH similar to that of the equilibration conditions, and when necessary, salts similar to those in the buffers used for equilibration are added.

In the present invention, flow-through fraction refers to fractions that are collected without being adsorbed to the column when the load fraction is applied onto the column (impurities are adsorbed to the column and the substance of interest is not adsorbed to the column). On the other hand, the elution fraction refers to fractions that are collected by buffer having higher salt concentration than that of the load fraction when the load fraction is applied onto the column (the substance of interest is adsorbed to the column and in some cases impurities are adsorbed as well).

Furthermore, in the present invention, the eluted fraction (eluate) containing an antibody with a pI of 3.0 to 8.0, which is obtained from the anion exchange chromatography resin, can be purified further by hydrophobic interaction chromatography.

Purification of an antibody-containing composition by a hydrophobic interaction chromatography resin is generally performed using a buffer having a pH of 4 to 9, which is Tris, BIS-TRIS, and histidine at a concentration of 1 mmol/L to 500 mmol/L with addition of chloride ions and acetate ions as the counter ions, and further addition of sodium chloride, potassium chloride, sodium sulfate, ammonium sulfate, sodium citrate, and arginine as necessary. Preferably, but without limitation, purification is performed using a column equilibrated with a buffer having a pH of 7 to 8, which is Tris at a concentration of 10 mmol/L to 500 mmol/L with addition of chloride ions or acetate ions as the counter ions, and further addition of sodium chloride and/or sodium sulfate at 50 mmol/L to 500 mmol/L as necessary.

The fractions containing the antibody of interest can be obtained as the flow-through fraction and/or the elution fraction of hydrophobic interaction chromatography by loading the eluted fraction from anion exchange chromatography obtained by the method of the present invention. Normally, the load fraction is adjusted in advance to have a pH similar to that of the equilibration conditions, and when necessary, salts similar to those in the buffers used for equilibration are added.

In methods of the present invention, by not including chloride ions in the compositions of the buffer and load fraction, effects of preventing rust in the buffer tank and the fraction tank can be expected.

In the methods of the present invention for removing impurities from a composition containing an antibody with a pI of 3.0 to 8.0, the composition loaded onto the anion exchange chromatography resin may be a composition purified by known purification methods such as Protein A column chromatography, before loading onto the anion exchange chromatography resin. The composition loaded onto the anion exchange resin may be a composition that has been subjected to the following steps (a) to (c):

(a) holding a composition containing an antibody with a pI of 3.0 to 8.0 in an acidic condition;
(b) neutralizing the acidic composition obtained in step (a); and
(c) removing aggregates from the neutralized composition obtained in step (b) after at least one hour following the neutralization.

In the case that impurities are proteins, whether impurities have been removed can be determined by size exclusion chromatography (SEC), without being limited thereto.

In the case of DNA, the determination can be carried out by a qPCR method, a threshold method, or such, without being limited thereto.

In the case of host cell protein (HCP), the determination can be carried out by ELISA that uses anti-HCP antibodies, without being limited thereto.

In the case of Protein A, the determination can be carried out by ELISA that uses anti-Protein A antibodies, without being limited thereto.

In the case of viruses, the determination can be carried out by a qPCR method, tissue infection method, plaque method, or such, without being limited thereto.

In the case of IGF, the determination can be carried out by ELISA that uses anti-IGF antibodies, without being limited thereto.

In the case of insulin, the determination can be carried out by ELISA that uses anti-insulin antibodies, without being limited thereto.

In the case of FL, the determination can be carried out by ELISA that uses anti-FL antibodies, without being limited thereto.

In the case of anti-foaming agents, the determination can be carried out by NMR, without being limited thereto.

In the case of endotoxin, the determination can be carried out by a colorimeteric method or turbidimetry based on the reaction that activates limulus amebocyte lysate (LAL), a component extracted from blood cells of horseshoe crab, without being limited thereto.

In the case of antibiotics, their concentrations can be determined by ELISA that uses antibodies which specifically recognize antibiotics such as gentamycin, without being limited thereto.

Furthermore, the present invention relates to a method for producing an antibody with a pI of 3.0 to 8.0, which comprises a step of removing antibody aggregates and/or impurities from a composition containing the antibody with a pI of 3.0 to 8.0. Furthermore, the present invention relates to a method for producing a composition containing an antibody with a pI of 3.0 to 8.0. This method comprises the steps of:

(a) obtaining a composition containing an antibody with a pI of 3.0 to 8.0; and
(b) purifying the antibody with a pI of 3.0 to 8.0 from the composition obtained in step (a) by using, for example, the purification method described herein.

Antibody purification includes removing antibody aggregates and/or impurities from antibody-containing compositions. The content ratio of aggregates contained in the composition obtained in the present invention which comprises an antibody with a pI of 3.0 to 8.0 is, for example, 5% or less, preferably 4% or less, and particularly preferably 3% or less, without being limited thereto. In the present invention, the content ratio of aggregates refers to the proportion of antibodies that form aggregates relative to the amount of antibodies contained in the composition.

Furthermore, the present invention relates to antibodies with a pI of 3.0 to 8.0, which are obtained by the purification methods or such or production methods described herein, or compositions comprising these antibodies. The present invention also relates to antibodies with a pI of 3.0 to 8.0, which are obtained by the purification methods or such or production methods described herein, or pharmaceutical compositions containing these antibodies. Pharmaceutical compositions of the present invention may comprise pharmaceutically acceptable carriers and/or additives.

Furthermore, the present invention relates to a method for producing a pharmaceutical composition containing an antibody with a pI of 3.0 to 8.0, which comprises the steps of: 1) obtaining an antibody with a pI of 3.0 to 8.0 by the method described herein; and 2) formulating the antibody with a pI of 3.0 to 8.0 produced in step 1) by mixing it with a pharmaceutically acceptable carrier and/or additive.

Pharmaceutical compositions of the present invention may be liquid formulations (antibody-containing liquid formulations) or lyophilized formulations. Liquid formulations of the present invention include solutions before lyophilizing in the production process for lyophilized formulations, or solutions after redissolving. The liquid formulations of the present invention are preferably liquid formulations produced without including a lyophilizing step in the production process. Lyophilized agents of the present invention can be obtained by lyophilizing the liquid formulations of the present invention by methods known to those skilled in the art.

Formulations of the present invention can include additives such as cryoprotective agents, suspending agents, solubilizing agents, isotonizing agents, preservatives, adsorption-preventing agents, diluents, excipients, pH adjusters, analgesics, sulfur-containing reducing agents, and antioxidants, and carriers as necessary.

Examples of cryoprotective agents include, but are not limited to, sugars such as trehalose, sucrose, and sorbitol.

Examples of solubilizing agents include, but are not limited to, polyoxyethylene hydrogenated castor oil, Polysorbate 80, nicotinic acid amide, polyoxyethylene sorbitan monolaurate, macrogol, and castor oil fatty acid ethyl ester.

Examples of isotonizing agents include, but are not limited to, sodium chloride, potassium chloride, and calcium chloride.

Examples of preservatives include, but are not limited to, methyl p-hydroxybenzoate, ethyl p-hydroxybenzoate, sorbic acid, phenol, cresol, and chlorocresol.

Examples of adsorption-preventing agents include, but are not limited to, human serum albumin, lecithin, dextran, ethyleneoxide-propyleneoxide copolymer, hydroxypropyl cellulose, methylcellulose, polyoxyethylene hydrogenated castor oil, and polyethylene glycol.

Examples of sulfur-containing reducing agents include, but are not limited to, N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and compounds with sulfhydryl groups such as thioalkanoic acids that have one to seven carbon atoms.

Examples of antioxidants include, but are not limited to, erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium hydrogen sulfite, sodium sulfite, triamyl gallate, and propyl gallate, or chelating agents such as disodium ethylenediamine tetraacetate (EDTA), sodium pyrophosphate, and sodium metaphosphate.

A formulation of the present invention can be administered either orally or parenterally, but generally, it is administered via a parenteral route. Specifically, it is administered by injection, transdermal, transmucosal, transnasal, transpulmonary administration, or such. Examples of the types of injections include subcutaneous injection, intravenous injection, intramuscular injection, and such which enable systemic or local administration. In the case of subcutaneous injection, there is a limit to the amount of injection solution, but the amount of antibody administered per injection can be a large amount (100 mg to 200 mg or so). Therefore, formulations of the present invention are particularly suitable for use in subcutaneous administration (injection).

All prior art documents cited in the specification are incorporated herein by reference.

EXAMPLES

Herein below, the present invention will be specifically described with reference to the Examples, but the scope of the invention is not limited to these Examples.

[Example 1] Suppression of Aggregate Formation in Subsequent Steps by Holding after Virus Inactivation and Neutralization The following antibodies were used in the Examples.

Mab1: an anti-IL-6 receptor antibody described in WO 2009/041621, whose pI has been changed to 5.8 by modifying the amino acids of Mab3. The amino acid sequences of the Mab1 antibody are H chain/SEQ ID NO: 1 and L chain/SEQ ID NO: 2.

Mab2: an anti-NR10 (IL-31 receptor) antibody, which is a fully humanized NS22 antibody produced by the method described in Example 12 of WO 2009/072604. The antibody class is IgG2, and is an antibody produced by lowering the pI to 5.6 through amino acid sequence modifications. The amino acid sequences of the Mab2 antibody are H chain/SEQ ID NO: 3 and L chain/SEQ ID NO: 4.

Mab3: tocilizumab (H chain/SEQ ID NO: 5 and L chain/SEQ ID NO: 6). The pI is 9.4.

The above-mentioned antibodies were expressed by methods known to those skilled in the art using a stable expression CHO cell line, then purified by a method known to those skilled in the art including protein A column chromatography, and then used for evaluation of aggregate removal in the following Examples.

By imitating a virus inactivation step in the actual production and purification process, purified antibody solutions of Mab1 and Mab2 were held at pH 3.8 or lower for 30 minutes or longer after addition of 1 mol/L hydrochloric acid. The held fractions were treated with 1 to 2 mol/L Tris for neutralization to pH 6.5 or higher. Fractions held for different lengths of time after neutralization were highly purified after removal of aggregates by methods known to those skilled in the art including hydroxyapatite column chromatography, or by methods including anion exchange chromatography. The aggregate-removed fractions were further held, and the amount of aggregates present according to the holding time after purification was calculated by the area percentage method using size exclusion chromatography (SEC).

As to hydroxyapatite column chromatography, with regard to Mab1, the column was equilibrated with 10 mmol/L phosphate buffer (pH 6.5), and then the neutralized fraction was loaded. After the column was washed with 10 mmol/L phosphate buffer (pH 6.5), the salt concentration was increased using 500 mmol/L NaCl, 10 mmol/L phosphate buffer (pH 6.5) to elute Mab1. With regard to Mab2, the column was equilibrated using 10 mmol/L phosphate buffer (pH 6.5), and then the neutralized fraction was loaded. After the column was washed with 100 mmol/L MES, 5 mmol/L phosphate buffer (pH 6.0), the salt concentration was increased using 200 mmol/L NaCl, 17.5 mmol/L phosphate buffer (pH 6.6) to elute Mab2.

As to anion exchange chromatography, with regard to Mab1, the column was equilibrated with 20 mmol/L Tris-acetate buffer (pH 8.0), and then the neutralized fraction was loaded. After the column was washed with 20 mmol/L Tris-acetate buffer (pH 8.0), the salt concentration was increased using 267 mmol/L Tris-acetate buffer (pH 8.0) to elute Mab1. With regard to Mab2, the column was equilibrated using 20 mmol/L Tris-HCl buffer (pH 7.0), and then the neutralized fraction was loaded. After the column was washed with 20 mmol/L Tris-HCl buffer (pH 7.0), the salt concentration was increased using 350 to 360 mmol/L NaCl, 20 mmol/L Tris-HCl buffer (pH 7.0 to 7.2) to elute Mab2.

Mab3 was similarly held with hydrochloric acid and then neutralized. The amount of aggregates formed during the holding time after neutralization was calculated.

Size exclusion chromatography (SEC) was carried out to analyze the amount of antibody aggregates present at each holding time. Each of the samples was diluted to approximately 1.0 g/L using the mobile phase described below, and they were analyzed using the G3000SWXL column (Tosoh). 50 mmol/L phosphate buffer (pH 7.5) containing 300 mmol/L NaCl was used for the mobile phase, and the analysis was performed at a flow rate of 0.5 mL/min. The peak that eluted before the monomer peak was analyzed as the aggregates, and the contents (%) of monomer and aggregates were calculated by the area percentage method.

The holding time after neutralization and the amount of aggregates after hydroxyapatite column chromatography (proportion of aggregates) for Mab1 and Mab2 are shown in Table 1. The amount of aggregates present after performing anion exchange chromatography is shown in Table 2. Regarding Mab1, Mab2, and Mab3, the amount of aggregates according to the holding time after neutralization is shown in Table 3. These results showed that in both Mab1 and Mab2, aggregates formed again if aggregates were removed by chromatography immediately after neutralization, whereas an increase in aggregates after the purification was hardly observed when purification was carried out after a certain time interval following neutralization. Meanwhile, an increase in aggregates after neutralization was not observed for Mab3, and one can conclude that holding time until the subsequent step is not necessary for Mab3.

TABLE 1

|      | Holding Time after Neutralization | Elapsed Time after Hydroxyapatite Column Chromatography | Aggregates Level |
|------|-----------------------------------|---------------------------------------------------------|------------------|
| Mab1 | 0 Hour                            | 0 Hour                                                  | 0.7%             |
|      |                                   | 6 Hours                                                 | 1.4%             |
|      |                                   | 24 Hours                                                | 1.9%             |
|      |                                   | 48 Hours                                                | 1.9%             |
|      | 24 Hours                          | 0 Hour                                                  | 0.0%             |
|      |                                   | 24 Hours                                                | 0.1%             |
|      | 66 Hours                          | 0 Hour                                                  | 0.0%             |
|      |                                   | 24 Hours                                                | 0.1%             |
| Mab2 | 0 Hour                            | 0 Hour                                                  | 0.1%             |
|      |                                   | 25 Hours                                                | 0.4%             |
|      |                                   | 48 Hours                                                | 0.4%             |
|      |                                   | 72 Hours                                                | 0.4%             |
|      | 20 Hours                          | 0 Hour                                                  | 0.1%             |
|      |                                   | 24 Hours                                                | 0.1%             |
|      |                                   | 55 Hours                                                | 0.1%             |
|      |                                   | 72 Hours                                                | 0.1%             |
|      | 24 Hours                          | 0 Hour                                                  | 0.0%             |
|      |                                   | 23 Hours                                                | 0.1%             |
|      |                                   | 49 Hours                                                | 0.1%             |
|      |                                   | 69 Hours                                                | 0.0%             |

TABLE 2

|      | Holding Time after Neutralization | Elapsed Time after Anion-exchange Column Chromatography | Aggregates Level |
|------|-----------------------------------|---------------------------------------------------------|------------------|
| Mab1 | 1.5 Hours                         | 0 Hour                                                  | 2.2%             |
|      |                                   | 4 Hours                                                 | 2.5%             |
|      |                                   | 24 Hours                                                | 2.7%             |
|      | 23 Hours                          | 0 Hour                                                  | 3.0%             |
|      |                                   | 24 Hours                                                | 3.0%             |
| Mab2 | 0 Hour                            | 0 Hour                                                  | 1.4%             |
|      |                                   | 24 Hours                                                | 3.5%             |
|      |                                   | 48 Hours                                                | 3.6%             |
|      | 6 Hours                           | 0 Hour                                                  | 0.7%             |
|      |                                   | 19 Hours                                                | 0.8%             |
|      | 24 Hours                          | 0 Hour                                                  | 0.8%             |
|      |                                   | 24 Hours                                                | 0.8%             |

TABLE 3

|      | Holding Time after Neutralization | Aggregates Level | Condition |
|------|-----------------------------------|------------------|-----------|
| Mab1 | 0.7 Hours                         | 15.54%           | ※1        |
|      | 6.7 Hours                         | 19.85%           |           |
|      | 9.7 Hours                         | 20.64%           |           |
|      | 12.7 Hours                        | 21.35%           |           |
|      | 24.7 Hours                        | 20.85%           |           |
|      | 0 Hours                           | 10.26%           | ※2        |
|      | 6 Hours                           | 15.02%           |           |
|      | 9 Hours                           | 15.75%           |           |
|      | 12 Hours                          | 16.33%           |           |
|      | 24 Hours                          | 16.38%           |           |
| Mab2 | 0 Hour                            | 2.73%            | ※3        |
|      | 2 Hours                           | 2.80%            |           |
|      | 4 Hours                           | 2.94%            |           |
|      | 5 Hours                           | 2.92%            |           |
|      | 6 Hours                           | 3.05%            |           |
|      | 7 Hours                           | 2.99%            |           |
|      | 8 Hours                           | 3.09%            |           |
|      | 9 Hours                           | 3.03%            |           |
|      | 0 Hour                            | 2.26%            | ※4        |
|      | 14 Hours                          | 3.36%            |           |
|      | 17 Hours                          | 3.36%            |           |
|      | 20 Hours                          | 3.41%            |           |
|      | 24 Hours                          | 3.50%            |           |

TABLE 3-continued

| | Holding Time after Neutralization | Aggregates Level | Condition |
|---|---|---|---|
| | 39 Hours | 3.48% | |
| | 49 Hours | 3.39% | |
| | 64 Hours | 3.48% | |
| Mab3 | 0 Hour | 0.90% | ※5 |
| | 2 Hours | 0.80% | |
| | 6 Hours | 0.80% | |
| | 24 Hours | 0.80% | |
| | 48 Hours | 0.70% | |

※1 One-hour holding at low pH 3.1 followed by neutralization to pH 7.0 (Acetic acid concentration in the antibody solution after purification on a Protein A column: 50 mM)
※2 One-hour holding at low pH 3.1 followed by neutralization to pH 7.0 (Acetic acid concentration in the antibody solution after purification on a Protein A column: 20 mM)
※3 One-hour holding at low pH 3.6 followed by neutralization to pH 7.0 (Acetic acid concentration in the antibody solution after purification on a Protein A column: 50 mM)
※4 One-hour holding at low pH 3.4 followed by neutralization to pH 7.0 (Acetic acid concentration in the antibody solution after purification on a Protein A column: 20 mM)
※5 One-hour holding at low pH 3.4 followed by neutralization to pH 7.0 (Hydrochloric acid concentration in the antibody solution after purification on a Protein A column: 2.5 mM)

[Example 2] Purification Process for Low-pI Antibodies

Example 2-1. Aggregates Removal in a Sodium Chloride-Containing Eluate of Mab1 with Anion Exchange Chromatography Mab1, an anti-IL-6 receptor antibody, is a genetically engineered antibody with low-pI (pI<8; pI 5.8). It was expressed by methods known to those skilled in the art using a stable expression CHO cell line, purified to high purity by a method known to those skilled in the art including Protein A column chromatography, and was used for purification in the following Example.

By imitating a virus-inactivation step in the production-scale purification process, the purified antibody solution of Mab1 was held at pH 3.6 or lower for 30 minutes or longer after addition of 1 mol/L hydrochloric acid. The held fraction was treated with 1 mol/L Tris for neutralization to pH 7 or higher. This was then held for 24 hours or longer, and then used for purification.

Purification was performed using the commercially available resins shown in Table 4 as anion exchange chromatography. The column was equilibrated with 20 mmol/L Tris-HCl buffer (pH 8.0), and then the neutralized fraction was loaded. After the column was washed with 20 mmol/L Tris-HCl buffer (pH 8.0), the salt concentration was increased using 20 mmol/L Tris-HCl, 100 to 150 mmol/L NaCl buffer (pH 8.0) to elute Mab1. The amount of aggregates after purification was calculated from size exclusion chromatography (SEC) by the area percentage method.

TABLE 4

YMC-BioPro
Q Sepharose High Performance
Q Sepharose Fast Flow
POROS HQ
Capto Q ImpRes Size exclusion chromatography (SEC) was carried out to analyze the amount of antibody aggregates present at each holding time. Each of the samples was diluted to approximately 1.0 g/L using the mobile phase described below, and they were analyzed using the G3000SWXL column (Tosoh). 50 mmol/L phosphate buffer (pH 7.5) containing 300 mmol/L NaCl was used for the mobile phase, and the analysis was performed at a flow rate of 0.5 mL/min. The peak that eluted earlier than the monomer peak was analyzed as the aggregate, and the contents (%) of monomer and aggregates were calculated by the area percentage method.

Regarding Mab1, the amount of aggregates present after purification by anion exchange chromatography is shown in Table 5. These results showed that monomer and aggregates of Mab1 were separated by anion exchange chromatography.

TABLE 5

| | Aggregates | |
|---|---|---|
| Anion-exchange Resin | Loaded Sample (%) | Eluted Fraction (%) |
| YMC-BioPro | 12.48 | 0.23 |
| Q Sepharose High Performance | 12.48 | 0.02 |
| Q Sepharose Fast Flow | 11.03 | 0.19 |
| POROS HQ | 10.99 | 0.02 |
| Capto Q ImpRes | 9.12 | 0.13 |

Example 2-2. Aggregates Removal by a Sodium Chloride-Containing Elution of Mab2 with Anion Exchange Chromatography Mab2, an anti-IL-31 receptor antibody, is a genetically engineered antibody with low-pI (pI<8; pI 5.6). It was expressed by methods known to those skilled in the art using a stable expression CHO cell line, purified to high purity by a method known to those skilled in the art including Protein A column chromatography, and was used for purification in the following Example.

By imitating a virus-inactivation step in the production-scale purification process, the purified antibody solution of Mab2 was held at pH 3.6 or lower for 30 minutes or longer after addition of 1 mol/L hydrochloric acid. The held fraction was treated with 1 mol/L Tris for neutralization to pH 7 or higher. This was then held for 20 hours or longer, and then used for purification.

Purification was performed using the commercially available resins shown in Table 6 as anion exchange chromatography. The column was equilibrated with 20 mmol/L Tris-HCl buffer (pH 7.0 or 8.0), and then the neutralized fraction was loaded. After the column was washed with 20 mmol/L Tris-HCl buffer (pH 7.0), the salt concentration was increased using 20 mmol/L Tris-HCl, 200 mmol/L to 300 mmol/L NaCl buffer (pH 7.0) to elute Mab2. The amount of aggregates after purification was calculated from size exclusion chromatography (SEC) by the area percentage method.

TABLE 6

POROS HQ
POROS PI

The amount of aggregates in Mab2 present after purification by anion exchange chromatography is shown in Table 7. These results showed that monomer and aggregates of Mab2 were separated by anion exchange chromatography.

TABLE 7

| Anion-exchange Resin | Aggregates | |
| --- | --- | --- |
| | Loaded Sample (%) | Eluted Fraction (%) |
| POROS HQ | 5.18 | 1.00 |
| POROS PI | 5.18 | 0.41 |

Example 2-3. Aggregates Removal in Various Elution of Mab1 by Anion Exchange Chromatography By imitating a virus-inactivation step in the production-scale purification process, the purified antibody solution of Mab1 was held at pH 3.6 or lower for 30 minutes or longer after addition of 1 mol/L HCl. The held fraction was treated with 1 mol/L Tris for neutralization to pH 7.0 or higher. This was then held for 24 hours or longer, and then used for purification.

Purification was performed using the commercially available resins shown in Table 8 as anion exchange chromatography. The column was equilibrated with 20 mmol/L Tris-HCl buffer (pH 8.0) or 20 mmol/L Tris-acetate buffer (pH 8.0), and then the neutralized fraction was loaded. After the column was washed with 20 mmol/L Tris-HCl buffer (pH 8.0) or 20 mmol/L Tris-acetate buffer (pH 8.0), the salt concentration was increased using 240 mmol/L to 270 mmol/L Tris-acetate buffer (pH 8.0), 40 mmol/L to 60 mmol/L sodium phosphate buffer (pH 8.0), or a buffer (pH 8.0) containing 20 mmol/L to 50 mmol/L sodium sulfate in 20 mmol/L Tris-HCl to elute Mab1. The amount of aggregates after purification was calculated from size exclusion chromatography (SEC) by the area percentage method.

TABLE 8

Q Sepharose Fast Flow
POROS HQ

Table 9 shows the amount of aggregates present in Mab1 after purification by anion exchange chromatography. These results showed that monomers and aggregates of Mab1 were separated by anion exchange chromatography.

TABLE 9

| Anion-exchange Resin | Salt Concentration in Elution | Aggregates | |
| --- | --- | --- | --- |
| | | Loaded Sample (%) | Eluted Fraction (%) |
| Q Sepharose Fast Flow | Tris-acetate: 243 mmol/L | 7.50 | 0.43 |
| POROS HQ | Tris-acetate: 265 mmol/L | 14.6 | 0.08 |
| Q Sepharose Fast Flow | Sodium Phosphate: 52 mmol/L | 14.92 | 0.23 |
| POROS HQ | Sodium Phosphate: 44 mmol/L | 14.92 | 0.02 |
| Q Sepharose Fast Flow | Sodium Sulfate: 40 mmol/L | 9.45 | 1.94 |
| POROS HQ | Sodium Sulfate: 29 mmol/L | 9.45 | 0.02 |

Example 2-4. Virus Clearance Capability with Tris-Containing Elution of Mab1 by Anion Exchange Chromatography By imitating a virus-inactivation step in the production-scale purification process, the purified antibody solution of Mab1 was held at pH 3.6 or lower for 30 minutes or longer after addition of 1 mol/L hydrochloric acid. The held fraction was treated with 1 mol/L Tris for neutralization to pH 7 or higher. This was then held for 20 hours or longer, and then used for purification.

Purification was performed using the commercially available POROS HQ resin (manufactured by Life Technologies) as anion exchange chromatography. The column was equilibrated with 20 mmol/L Tris-acetate buffer (pH 7.8) and then the neutralized fraction, to which a model retrovirus MuLV was added, was loaded. After the column was washed with 20 mmol/L Tris-acetate buffer (pH 7.8), the salt concentration was increased using 225 mmol/L to 275 mmol/L Tris-acetate buffer (pH 7.8) to elute Mab1. The amount of virus was calculated by determining the virus titer in the loaded fraction and the eluted fraction after purification.

The virus clearance capability by purification of Mab1 with anion exchange chromatography is shown in Table 10. The results show that viruses were removed effectively through purification with anion exchange chromatography using Tris-acetate.

TABLE 10

| Tris Concentration | Loaded Sample ($Log_{10}$ $TCID_{50}$) | Eluted Fraction ($Log_{10}$ $TCID_{50}$) | Clearance Capability ($Log_{10}$) |
| --- | --- | --- | --- |
| 225 mmol/L | 7.37 | ≤0.79 | ≥6.58 |
| 275 mmol/L | 7.07 | ≤0.55 | ≥6.53 |

Example 2-5. Aggregates Removal in Tris-Containing Elution of Mab2 with Anion Exchange Chromatography By imitating a virus-inactivation step in the actual production-scale purification process, the purified antibody solution of Mab2 was held at pH 3.6 or lower for 30 minutes or longer after addition of 1 mol/L hydrochloric acid. The held fraction was treated with 1 mol/L Tris for neutralization to pH 7 or higher. This was then held for 20 hours or longer, and then used for purification.

Purification was performed using the commercially available resins shown in Table 11 as anion exchange chromatography. The column was equilibrated with 20 mmol/L Tris-HCl buffer (pH 7.0 or 8.0) and then the neutralized fraction was loaded. After the column was washed with 20 mmol/L Tris-acetate buffer (pH 7.0 or 8.0), the salt concentration was increased using 300 mmol/L to 500 mmol/L Tris-acetate (pH 7.0 or 8.0) to elute Mab2. The amount of aggregates after purification was calculated from size exclusion chromatography (SEC) by the area percentage method.

TABLE 11

POROS HQ
POROS PI

Table 12 shows the amount of aggregates present in Mab2 after purification with anion exchange chromatography. These results showed that monomer and aggregates of Mab2 were separated by anion exchange chromatography.

TABLE 12

| Anion-exchange Resin | Tris-acetate Concentration in Elution | Aggregates Loaded Sample (%) | Aggregates Eluted Fraction (%) |
|---|---|---|---|
| POROS HQ | 343 mmol/L | 7.16 | 0.93 |
| POROS PI | 441 mmol/L | 5.18 | 0.39 |

Example 2-6. Virus Clearance Capability with Tris-Containing Elution of Mab2 by Anion Exchange Chromatography By imitating a virus-inactivation step in the actual production-scale purification process, the purified antibody solution of Mab2 was held at pH 3.6 or lower for 30 minutes or longer after addition of 1 mol/L hydrochloric acid. The held fraction was treated with 1 mol/L Tris for neutralization to pH 7 or higher. This was then held for 20 hours or longer, and then used for purification.

Purification was performed using the commercially available POROS PI resin (manufactured by Life Technologies) as anion exchange chromatography. The column was equilibrated with 20 mmol/L Tris-HCl buffer (pH 8.0) and then the neutralized fraction, to which a model retrovirus MuLV was added, was loaded. After the column was washed with 20 mmol/L Tris-HCl buffer (pH 8.0), the salt concentration was increased using 470 mmol/L Tris-HCl buffer (pH 8.0) to elute Mab2. The amount of virus was calculated by determining the virus titer in the loaded fraction and the eluted fraction after purification.

The virus clearance capability by purification of Mab2 with anion exchange chromatography is shown in Table 13. The results show that viruses were removed through purification with anion exchange chromatography using Tris-HCl.

TABLE 13

| Tris Concentration | Loaded Sample ($Log_{10}$ $TCID_{50}$) | Eluted Fraction ($Log_{10}$ $TCID_{50}$) | Clearance Capability ($Log_{10}$) |
|---|---|---|---|
| 470 mmol/L | 7.56 | 4.12 | 3.44 |

Example 2-7. Purification of Mab1 by Anion Exchange Chromatography and Multimodal Chromatography Mab1 was expressed by a method known to those skilled in the art using a stable expression CHO cell line, purified to high purity by a method known to those skilled in the art including Protein A column chromatography, followed by subsequent purification with anion exchange chromatography shown in Examples 2-3 and 2-4, and then used for purification in the following Example.

The eluted fractions from anion exchange chromatography were adjusted to pH 6.5+/−0.3 using acetic acid. Purification was carried out by multimodal chromatography (hydrophobic+anion exchange) using the commercially available Capto Adhere resin (manufactured by GE Healthcare). After the column was equilibrated using 250+/−25 mmol/L Tris-acetate buffer (pH 6.5), the pH-adjusted fractions were loaded. Mab1 in the Flow-through fraction was collected.

This series of purification steps enabled removal of DNA to <1.0 pg/mg-Mab1 (under the quantification limit), host cell proteins to <17 ng/mg-Mab1 (under the quantification limit), and leached Protein A to <0.4 ng/mg-Mab1 (under the quantification limit), which are process-derived impurities, and also removal of Mab1 aggregates as shown in Example 2-3. Regarding virus clearance capability, in addition to the sufficient virus clearance capability demonstrated in Example 2-4, a high virus clearance capability of 5.42 $Log_{10}$ could be guaranteed for the model retrovirus MuLV by the multimodal chromatography step.

DNA was measured by quantitative PCR. Host cell proteins were measured by ELISA using anti-host cell proteins antibody. Leached Protein A was measured by ELISA using an anti-Protein A antibody.

Example 2-8. Purification of Mab2 by Anion Exchange Chromatography and Hydrophobic Interaction Chromatography Mab2 was expressed by a method known to those skilled in the art using a stable expression CHO cell line, purified to high purity by a method known to those skilled in the art including Protein A column chromatography, followed by subsequent purification with anion exchange chromatography shown in Examples 2-2 and 2-6, and then used for purification in the following Example.

Salt (for example sodium sulfate) was added at a final concentration of 250 mmol/L or more to the eluted fractions from anion exchange chromatography, and the pH was adjusted to 6.8 to 8.0. Purification was carried out using a hydrophobic interaction chromatography resin (for example, a resin carrying phenyl groups). After equilibration using a buffer (pH 6.8 to 8.0) with an equivalent concentration to the added salt, the fractions were loaded and Mab2 in the Flow-through fraction was collected.

This series of purification steps enabled removal of DNA to 1.9 pg/mg-Mab2, host cell proteins to <8.0 ng/mg-Mab2 (under the quantification limit), and leached Protein A to <0.4 ng/mg-Mab2 (under the quantification limit), which are process-derived impurities, and also removal of Mab2 aggregates as shown in Example 2-2. Regarding virus clearance capability, in addition to the sufficient virus clearance capability demonstrated in Example 2-6, a high virus clearance capability of 5.94 $Log_{10}$ and 1.55 $Log_{10}$ could be guaranteed for the model retrovirus MuLV and the model parvovirus MVM, respectively, by the hydrophobic interaction chromatography step.

DNA was measured by quantitative PCR. Host cell proteins were measured by ELISA using anti-host cell proteins antibody. Leached Protein A was measured by ELISA using an anti-Protein A antibody.

[Example 3] Aggregates Formation Depending on the Difference in Holding pH after Neutralization Following Virus Inactivation The following antibody was used in this Example.

Mab1: an anti-IL-6 receptor antibody described in WO 2009/041621, whose pI has been changed to 5.8 by modifying the amino acids of Mab3. The amino acid sequences of the Mab1 antibody are H chain/SEQ ID NO: 1 and L chain/SEQ ID NO: 2.

The above-mentioned antibody was expressed by methods known to those skilled in the art using a stable expression CHO cell line, purified by a method known to those skilled in the art including Protein A column chromatography, and then used for evaluation of the amount of aggregate formation in the following Example.

By imitating a virus-inactivation step in the actual production-scale purification process, the purified antibody solution of Mab1 was held at pH 3.8 or lower for 30 minutes or longer after addition of 1 mol/L hydrochloric acid. The held fraction was treated with 2 mol/L Tris for neutralization to pH 5.0 which is lower than the antibody pI, and to pH 7.0 which is higher than the antibody pI. After neutralization, samples were collected over time, and the amount of aggregates was determined. Furthermore, the sample neutralized to pH 5.0 was held for 22 hours after the neutralization, and then 2 mol/L Tris was additionally added to hold the pH at 7.0 which is higher than the antibody pI. Samples were collected over time, and the amount of aggregates was determined. The amount of aggregates was calculated from the size exclusion chromatography (SEC) by the area percentage method.

Size exclusion chromatography (SEC) was carried out to analyze the amount of antibody aggregates present at each holding time. Each of the samples was diluted to approximately 1.0 g/L using the mobile phase described below, and they were analyzed using the G3000SWXL column (Tosoh). 50 mmol/L phosphate buffer (pH 7.5) containing 300 mmol/L NaCl was used for the mobile phase, and the analysis was performed at a flow rate of 0.5 ml/min. The peak that eluted earlier than the monomer peak was analyzed as the aggregate, and the contents (%) of monomer and aggregates were calculated by the area percentage method.

The amount of increase in aggregates over time when the antibodies were held at pH 7.0, and the amount of increase in aggregates over time when the antibodies were held at pH 5.0 for 22 hours and then held at pH 7.0 are shown respectively in Table 14 (when held at pH 7.0) and Table 15 (when retained at pH 5.0 for 22 hours, followed by increase of the pH to 7.0). These results showed that even if the increase of aggregates over time becomes saturated after neutralizing Mab1 to pH 5.0 (lower than the pI of Mab1), once the pH is raised to pH 7.0 (higher than the pI of Mab1) followed by holding, an increase in aggregates over time is observed again, and this becomes re-saturated after holding for a certain period of time.

TABLE 14

| Neutralizing pH | Holding Time after Neutralization | Aggregates Level |
| --- | --- | --- |
| pH 7.0 | 0 Hour | 3.8% |
|  | 2 Hours | 5.4% |
|  | 4 Hours | 6.2% |
|  | 6 Hours | 7.0% |
|  | 22 Hours | 7.9% |
|  | 48 Hours | 8.9% |

TABLE 15

| Neutralizing pH | Holding Time after Neutralization | Aggregates Level |
| --- | --- | --- |
| pH 5.0 | 0 Hour | 2.8% |
|  | 2 Hours | 4.7% |
|  | 4 Hours | 5.5% |
|  | 6 Hours | 5.7% |
|  | 22 Hours | 5.9% |
| pH 7.0 | 0 Hour | 5.4% |
|  | 2 Hours | 6.4% |
|  | 4 Hours | 6.6% |
|  | 7.5 Hours | 7.2% |
|  | 26 Hours | 7.3% |
|  | 48 Hours | 7.8% |

INDUSTRIAL APPLICABILITY

The present invention provides purification methods for efficiently removing antibody aggregates and impurities in a composition containing a low-pI antibody in particular. The present invention enables to provide drug product containing an antibody with less-aggregate formation. Purification methods of the present invention are useful in the production of biological medicinal product for which high purity is required.

The invention claimed is:

1. A method for purifying a composition containing an antibody with a pI of 3.0 to 8.0, which comprises the steps of:
   (a) treating the composition containing the antibody with a pI of 3.0 to 8.0 with an acidic condition;
   (b) neutralizing the acidic composition obtained in step (a);
   (c) holding the neutralized composition obtained in step (b) at least one hour; and
   (d) removing aggregates from the neutralized composition after step (c), wherein step (a) is a virus-inactivating treatment step performed after Protein A column chromatography purification of the antibody with a pI of 3.0 to 8.0.

2. The method of claim 1, wherein the aggregate removal is carried out by anion exchange chromatography, hydrophobic interaction chromatography, multimodal chromatography, or hydroxyapatite chromatography.

3. The method of claim 1, wherein the pI of the antibody is 5.0 to 7.5.

4. The method of claim 1, wherein the pI of the antibody is 5.0 to 6.5.

5. The method of claim 1, wherein aggregates removal is carried out by a method for removing impurities from a composition containing an antibody with a pI of 3.0 to 8.0, which includes the steps of:
   (i) loading the composition containing the antibody with a pI of 3.0 to 8.0 onto an anion exchange resin; and
   (ii) eluting the antibody with a pI of 3.0 to 8.0 from the anion exchange resin with the Bind/Elute mode using an eluting solution that has a salt concentration higher than that of the composition of (i).

6. The method of claim 1, wherein the antibody is a humanized antibody or a human antibody.

7. The method of claim 1, wherein the antibody is an anti-IL-6 receptor antibody or an anti-IL-31 receptor antibody.

8. A method for producing a composition containing an antibody with a pI of 3.0 to 8.0, in which the content ratio of the antibody aggregates are 3% or less, by performing the method of claim 1.

9. A method for producing a pharmaceutical composition containing an antibody with a pI of 3.0 to 8.0, which includes the steps of:
   (a) purifying an antibody with a pI of 3.0 to 8.0 by the steps of:
      (i) treating the composition containing the antibody with a pI of 3.0 to 8.0 with an acidic condition;
      (ii) neutralizing the acidic composition obtained in step (i);
      (iii) holding the neutralized composition obtained in step (ii) at least one hour; and
      (iv) removing aggregates from the neutralized composition after step (iii); wherein step (i) is a virus-inactivating treatment step performed after Protein A column chromatography purification of the antibody with a pI of 3.0 to 8.0; and
   b) mixing the antibody with a pI of 3.0 to 8.0 from step a) with a pharmaceutically acceptable carrier and/or additive, thereby producing the pharmaceutical composition containing an antibody with a pI of 3.0 to 8.0.

10. A method for removing an antibody aggregate from a composition containing an antibody with a pI of 3.0 to 8.0, which includes the steps of:
    (a) treating the composition containing an antibody with a pI of 3.0 to 8.0 with an acidic condition;
    (b) neutralizing the acidic composition obtained in step (a);
    (c) holding the neutralized composition obtained in step (b) at least one hour; and
    (d) removing aggregates from the neutralized composition.

11. A method for purifying a composition containing an antibody with a pI of 3.0 to 8.0, which includes the steps of:
    (a) treating the composition containing an antibody with a pI of 3.0 to 8.0 with an acidic condition;
    (b) neutralizing the acidic composition obtained in step (a); and
    (c) holding the neutralized composition obtained in step (b) at least one hour; and
    (d) removing aggregates from the neutralized composition step (c).

* * * * *

SEQUENCE LISTING

```
<160> NUMBER OF SEQ ID NOS: 6

<210> SEQ ID NO 1
<211> LENGTH: 443
<212> TYPE: PRT
<213> ORGANISM: Artificial Sequence
<220> FEATURE:
<223> OTHER INFORMATION: An artificially synthesized peptide sequence

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                 85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
        435                 440

<210> SEQ ID NO 2
<211> LENGTH: 214
<212> TYPE: PRT
<213> ORGANISM: Artificial Sequence
<220> FEATURE:
<223> OTHER INFORMATION: An artificially synthesized peptide sequence

<400> SEQUENCE: 2

```
Asp Ile Gln Met Thr Gln Ser Pro Ser Ser Leu Ser Ala Ser Val Gly
 1               5                  10                  15

Asp Ser Val Thr Ile Thr Cys Gln Ala Ser Thr Asp Ile Ser Ser His
             20                  25                  30

Leu Asn Trp Tyr Gln Gln Lys Pro Gly Lys Ala Pro Glu Leu Leu Ile
         35                  40                  45

Tyr Tyr Gly Ser His Leu Leu Ser Gly Val Pro Ser Arg Phe Ser Gly
 50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gly Gln Gly Asn Arg Leu Pro Tyr
                 85                  90                  95

Thr Phe Gly Gln Gly Thr Lys Val Glu Ile Glu Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
            210
```

<210> SEQ ID NO 3
<211> LENGTH: 445
<212> TYPE: PRT
<213> ORGANISM: Artificial Sequence
<220> FEATURE:
<223> OTHER INFORMATION: An artificially synthesized peptide sequence

<400> SEQUENCE: 3

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
             20                  25                  30

Ile Met Asn Trp Val Arg Gln Ala Pro Gly Gln Gly Leu Glu Trp Met
         35                  40                  45

Gly Leu Ile Asn Pro Tyr Asn Gly Gly Thr Asp Tyr Asn Pro Gln Phe
     50                  55                  60

Gln Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Tyr Asp Asp Gly Pro Tyr Thr Leu Gly Thr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
        290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445

<210> SEQ ID NO 4
<211> LENGTH: 214
<212> TYPE: PRT
<213> ORGANISM: Artificial Sequence
<220> FEATURE:
<223> OTHER INFORMATION: An artificially synthesized peptide sequence

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Phe
            20                  25                  30

Val Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Tyr Asp Ser Pro Leu
             85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 5
<211> LENGTH: 449
<212> TYPE: PRT
<213> ORGANISM: Artificial Sequence
<220> FEATURE:
<223> OTHER INFORMATION: An artificially synthesized peptide sequence

<400> SEQUENCE: 5

Gln Val Gln Leu Gln Glu Ser Gly Pro Gly Leu Val Arg Pro Ser Gln
  1               5                  10                  15

Thr Leu Ser Leu Thr Cys Thr Val Ser Gly Tyr Ser Ile Thr Ser Asp
             20                  25                  30

His Ala Trp Ser Trp Val Arg Gln Pro Pro Gly Arg Gly Leu Glu Trp
         35                  40                  45

Ile Gly Tyr Ile Ser Tyr Ser Gly Ile Thr Thr Tyr Asn Pro Ser Leu
 50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
             85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205
```

Ser Asn Thr Lys Val Asp Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
        245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 6
<211> LENGTH: 214
<212> TYPE: PRT
<213> ORGANISM: Artificial Sequence
<220> FEATURE:
<223> OTHER INFORMATION: An artificially synthesized peptide sequence

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

-continued

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```